US00PP26483P3

(12) United States Plant Patent
Jandrew

(10) Patent No.: US PP26,483 P3
(45) Date of Patent: Mar. 8, 2016

(54) ***CALIBRACHOA* PLANT NAMED 'PAS1020307'**

(50) Latin Name: *Calibrachoa×hybrida*
Varietal Denomination: PAS1020307

(71) Applicant: Ball Horticultural Company, West Chicago, IL (US)

(72) Inventor: Jason Jandrew, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 114 days.

(21) Appl. No.: 14/120,752

(22) Filed: Jun. 23, 2014

(65) Prior Publication Data

US 2015/0373893 P1 Dec. 24, 2015

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Annette Para
(74) *Attorney, Agent, or Firm* — Audrey Charles

(57) ABSTRACT

A new and distinct cultivar of *Calibrachoa* plant named 'PAS1020307', characterized by its white-colored flowers, medium green-colored foliage, moderately vigorous, mounded-trailing growth habit, is disclosed.

1 Drawing Sheet

Latin name of genus and species of plant claimed: *Calibrachoa×hybrida.*

Variety denomination: 'PAS1020307'.

BACKGROUND OF THE INVENTION

The present invention relates to a new and distinct cultivar of *Calibrachoa* plant botanically known as *Calibrachoa× hybrida* and hereinafter referred to by the cultivar name 'PAS1020307'.

The new cultivar originated in a controlled breeding program in Elburn, Ill. during February 2012. The objective of the breeding program was the development of *Calibrachoa* cultivars with unique flower coloration and mounded-trailing growth habit.

The new *Calibrachoa* cultivar is the result of cross-pollination. The female (seed) parent of the new cultivar is the proprietary *Calibrachoa×hybrida* breeding selection coded N7734R, not patented, characterized by its white-colored flowers, medium green-colored foliage, and moderately vigorous, prostrate growth habit. The male (pollen) parent of the new cultivar is the proprietary *Calibrachoa×hybrida* breeding selection coded N7606R, not patented, characterized by its white-colored flowers, medium green-colored foliage, and moderately vigorous, compact-mounded growth habit. The new cultivar was discovered and selected as a single flowering plant within the progeny of the above stated cross-pollination during July 2012 in a controlled environment in Elburn, Ill.

Both parents have a degree of homozygosity such that the progeny of the cross N7734R times N7606R are phenotypically uniform and essentially identical to 'PAS1020307'. Accordingly, phenotypically identical 'PAS1020307' can be produced by sexual reproduction as well as asexual reproduction.

Asexual reproduction of the new cultivar by terminal stem cuttings since July 2012 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'PAS1020307' as a new and distinct cultivar of *Calibrachoa* plant:

1. White-colored flowers;
2. Medium green-colored foliage;
3. Moderately vigorous, mounded-trailing growth habit.

Plants of the new cultivar differ from plants of the female parent primarily in growth habit. Plants of the new cultivar differ from plants of the male parent primarily in having larger-sized flowers and a trailing growth habit.

Of the many commercially available *Calibrachoa* cultivars, the most similar in comparison to the new cultivar is CABARET White Improved 'Balcabwhite', not patented. However, in side by side comparisons, plants of the new cultivar differ from plants of 'Balcabwhite' in at least the following characteristics:

1. Plants of the new cultivar have larger leaves, as measured by length and width, than plants of 'Balcabwhite'; and
2. Plants of the new cultivar are taller than plants of 'Balcabwhite'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'PAS1020307'. The plants were grown in 4.5-inch pots for 5 weeks in a greenhouse in West Chicago, Ill. Plants were given one pinch one week before transplant.

DETAILED BOTANICAL DESCRIPTION

Figure 1:
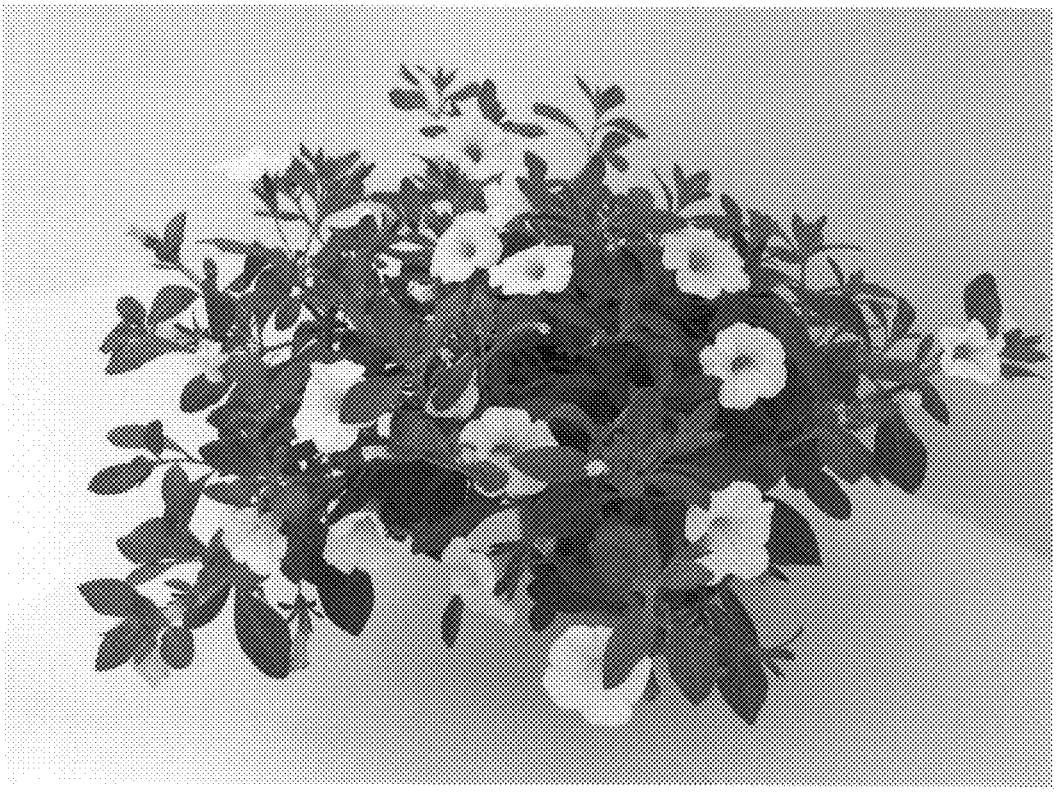
FIG. 1 illustrates a side view of the overall growth and flowering habit of 'PAS1020307'.
Figure 2:
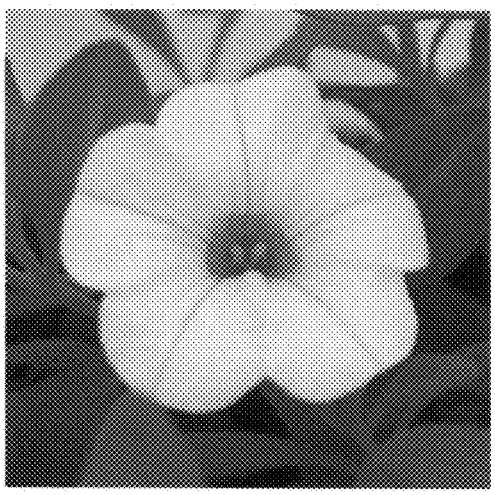
FIG. 2 illustrates a close-up view of an individual flower of 'PAS1020307'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2014 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 5 weeks utilizing a soilless growth medium. Plants were given one pinch one week before transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Calibrachoa×hybrida* cultivar PAS1020307.

Parentage:

*Female parent*.—Proprietary *Calibrachoa×hybrida* breeding selection coded N7734R, not patented.

*Male parent*.—Proprietary *Calibrachoa×hybrida* breeding selection coded N7606R, not patented.

Propagation:

*Type cutting*.—Terminal stem.

*Time to initiate roots*.—Approximately 6 to 8 days.

*Time to produce a rooted cutting*.—Approximately 24 to 28 days.

*Root description*.—Fibrous.

*Rooting habit*.—Freely branching.

Plant description:

*Commercial crop time*.—Approximately 4 to 6 weeks from a rooted cutting to finish in a 10 cm pot.

*Growth habit and general appearance*.—Moderately vigorous, mounded-trailing.

*Size*.—Height from soil level to top of plant plane: Approximately 11.0 cm. Width: Approximately 34.5 cm.

*Branching habit*.—Freely branching, pinching enhances basal branching. Quantity of main branches per plant: Approximately 4.

*Branch*.—Strength: Strong, flexible. Length: Approximately 21.0 cm. Diameter: Approximately 2.0 mm. Length of central internode: Approximately 1.0 cm. Texture: Densely glandular pubescent. Gland color: Colorless, transparent. Color of young and mature stems: 144A.

Foliage description:

*General description*.—Quantity of leaves per main branch: Approximately 18. Fragrance: Slight. Form: Simple. Arrangement on flowering stem: Opposite.

*Leaves*.—Aspect: At acute angle to stem with tip turning downward. Shape: Elliptic. Margin: Entire. Apex: Broadly acute. Base: Attenuate. Venation pattern: Pinnate. Length of mature leaf: Approximately 3.6 cm. Width of mature leaf: Approximately 1.7 cm. Texture of upper and lower surfaces: Moderately pubescent with a mixture of glandular hairs. Gland color: Colorless, transparent. Color of upper surface of young and mature foliage: 137B with midvein of 144D. Color of lower surface of young and mature foliage: Closest to 138B with midvein of 138C.

*Petiole*.—Length: Approximately 7.0 mm. Diameter: Approximately 2.0 mm. Texture: Moderately glandular pubescent. Gland color: Colorless, transparent. Color: 144A.

Flowering description:

*Flowering habit*.—'PAS1020307' is freely flowering under outdoor growing conditions with substantially continuous blooming from spring through autumn and year-round in greenhouse environment.

*Lastingness of individual flower on the plant*.—Approximately 5 to 7 days.

Flower description:

*General description*.—Type: Single, salverform. Quantity per plant: Approximately 17. Fragrance: None detected.

*Bud*.—Rate of opening: Generally takes 3 to 4 days for bud to progress from first color to fully open flower. Quantity per plant: Approximately 18.

*Bud just before opening*.—Shape: Oblong. Length: Approximately 1.7 cm. Diameter: Approximately 5.0 mm. Texture: Densely glandular pubescent. Gland color: Colorless, transparent. Color: Petal portion 155B and tube portion 150B, venation of 145B.

*Corolla*.—Diameter: Approximately 3.2 cm.

*Petals*.—Quantity: 5, fused to form a tube. Shape: Obovate. Margin: Entire. Apex: Obtuse. Length from tube: Approximately 1.4 cm. Length of free portion: Approximately 5.0 mm. Width: Approximately 1.6 cm. Texture of upper surface: Glabrous. Texture of lower surface: Glandular pubescent, dense along venation. Gland color: Colorless, transparent. Color of upper surface when first and fully open: NN155D with midveins of 145B. Color of lower surface when first and fully open: NN155D with midveins of 145C.

*Corolla tube*.—Length: Approximately 1.7 cm. Diameter at distal end: Approximately 6.0 mm. Diameter at proximal end: Approximately 1.0 mm. Texture of inner surface: Glabrous. Texture of outer surface: Densely glandular pubescent. Gland color: Colorless, transparent. Color of inner surface: 150C with venation of 145A. Color of outer surface: 150C with venation of 145B.

*Sepals*.—Quantity per flower: 5, fused along lower half. Shape: Lanceolate. Apex: Acute. Length: Approximately 1.4 cm. Width: Approximately 2.0 mm. Texture of upper and lower surfaces: Densely glandular pubescent. Gland color: Colorless, transparent. Color of upper surface: 137A. Color of lower surface: 137B with base of 144B.

*Peduncle*.—Strength: Strong, flexible. Aspect: Acute angle to stem. Length: Approximately 1.9 cm. Diameter: Approximately 1.0 mm. Texture: Densely glandular pubescent. Gland color: Colorless, transparent. Color: 144A.

*Reproductive organs*.—Androecium: Stamen quantity: 5, basifixed. Stamen length: Approximately 9.0 mm. Filament length of fixed portion: Approximately 4.0 mm. Filament color: 145D. Anther shape: Bilobed, ovoid. Anther length: Approximately 1.0 mm. Anther color: 8A. Pollen amount: Abundant. Pollen color: 8C. Gynoecium: Pistil quantity: 1 per flower. Pistil length: Approximately 1.0 cm. Stigma shape: Funnel. Stigma length: Less than 1.0 mm. Stigma color: 144A. Style length: Approximately 8.0 mm. Style color: N145B. Ovary length: Approximately 2.0 mm. Ovary color: N144D.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'PAS1020307', substantially as herein shown and described.

* * * * *